US00PP10725P

United States Patent [19]

Barth

[11] Patent Number: Plant 10,725

[45] Date of Patent: Dec. 15, 1998

[54] ECHINODORUS PLANT NAMED 'RED FLAME'

[76] Inventor: Hans Barth, Ruhrstr. 30, 06846 Dessau, Germany

[21] Appl. No.: 853,795

[22] Filed: May 9, 1997

[51] Int. Cl.[6] ..... A01H 5/00

[52] U.S. Cl. ..... Plt./87.16

[58] Field of Search ..... Plt./87.16

*Primary Examiner*—Howard J. Locker
*Assistant Examiner*—Kent L. Bell
*Attorney, Agent, or Firm*—C. A. Whealy

[57] ABSTRACT

A distinct cultivar of Echinodorus plant named 'Red Flame', characterized by its relatively compact plant habit; moderate vigor and moderate growth rate; and attractive dark green leaves with numerous dark brownish red spots and blotches.

2 Drawing Sheets

The present invention relates to a new and distinct cultivar of Echinodorus plant, botanically known as *Echinodorus horemanii red×schlueteri,* and hereinafter referred to by the cultivar name 'Red Flame' .

The new cultivar is a product of a planned breeding program conducted by the inventor in Dessau, Germany. The new cultivar was discovered by the inventor as a naturally-occurring mutation of the nonpatented Echinodorus cultivar 'Ozelot' in a controlled environment in Dessau, Germany, in May, 1996. The cultivar 'Ozelot' originated from a cross by the inventor between an unnamed plant of *Echinodorus horemanii red* as the female or seed parent and the nonpatented cultivar *Echinodorus schlueteri* 'Leopard' as the male or pollen parent. The cultivar 'Red Flame' was selected from a population of plants of the cultivar 'Ozelot' based on its desirable leaf color.

The new Echinodorus differs from its parent, the cultivar 'Ozelot', in leaf color. Plants of the new Echinodorus have more dark brownish red spots and blotches than plants of the cultivar 'Ozelot'. The increased incidence of spotting/blotching on plants of the new Echinodorus gives a dark reddish overall appearance to the leaves compared to the green overall coloration of leaves of plants of the cultivar 'Ozelot'.

Asexual propagation of the new cultivar by tissue culture at Dessau, Germany, has shown that the unique features of this new Echinodorus plant are stable and reproduced true to type in successive generations of asexual propagation.

The new Echinodorus has not been observed under all possible environmental conditions. The phenotype may vary somewhat with variations in environment such as temperature and light intensity, without, however, any variance in genotype. In addition, the appearance of plants grown in an aerial environment may differ from the appearance of plants grown in an aquatic environment. The following observations, measurements and comparisons describe plants grown in Berlin, Germany, in a glass greenhouse in an aquatic environment with average day and night temperatures of 25° C. The new Echinodorus can only be grown in fresh water. A pH of 6.5 to 7.8 and me/L of less than 30 are recommended for optimum growth.

The following traits have been repeatedly observed and are determined to be the unique characteristics of 'Red Flame'. These characteristics in combination distinguish 'Red Flame' as a new and distinct cultivar:

1. Relatively compact plant habit.
2. Moderate vigor and moderate growth rate.
3. Attractive green leaves with numerous dark brownish red spots and blotches.

The accompanying colored photographs illustrate the overall appearance of the new cultivar, showing the colors as true as it is reasonably possible to obtain in colored reproductions of this type.

The first photograph comprises a top perspective view of a typical plant of 'Red Flame' in an aquatic environment. The second photograph comprises a top perspective view of a typical young plant of 'Red Flame' showing both the upper and lower surfaces of the leaves.

Foliage colors in the photographs may appear different from the actual colors due to light reflectance.

In the following description, color references are made to The Royal Horticultural Society Colour Chart except where general terms of ordinary dictionary significance are used.

Botanical classification: *Echinodorus horemanii red× schlueteri* cultivar 'Red Flame'.

Parentage: Naturally-occurring mutation of *Echinodorus horemanii red ×schlueteri* cultivar 'Ozelot'.

Propagation: By tissue culture and by adventitious shoots. Plants grown in aerial or aquatic environments will develop thick, white, tapered roots with many fine lateral roots.

Plant description:

*Plant shape.*—Upright, inverted triangle, symmetrical.

*Growth habit.*—Rosette with leaves erect or slightly bent. Runners, or adventitious shoots, and rhizomes may form.

*Plant height.*—Relatively compact, about 27 cm from plant base to top of leaf plane.

*Plant vigor.*—Moderate.

*Growth rate*: Moderate.

*Crop time:* About 8 weeks are required from an adventitious shoot to a 5-cm pot.

*Foliage description.*—Arrangement: Single leaves arranged in a rosette on long petioles. Quantity of leaves per finished plant: on average, about nine. Leaf shape: Elliptic to obovate/oblanceolate. Leaf apex: Acute to rounded. Leaf base: Obtuse to cuneate. Venation: Palmate, usually 3 or 5 primary veins with secondary veins arranged in a herringbone pattern from the central vein and extending to the margin crossing through the longitudinal veins. Veins on lower leaf surface prominent. Vein color consistently similar to yellowish-green ground color of the leaf. Margin: Entire. Leaf aspect: Some undulation. Leaf texture: Glabrous. Glossy when wet, dull when dry leaves thin, translucent. Leaf size: Length: About 14 cm. Width: About 7 cm. Leaf color: Polymorphic. Actual leaf color is a function of the environment. In an aerial environment, leaf coloration is in tones of green. When grown in an aquatic environment, leaf colors are variegated and variable depending on leaf maturity. Spots and blotches are variable from leaf to leaf and do not extend over the veins. Immature leaves are more uniformly covered with brownish red color over a yellowish-green ground color. Older leaves are predominantly green with discontinuous spots or blotches of brownish red. Increasing light intensity will also increase the brownish red coloration. Young foliage, upper surface: More intense dark brownish red coloration than mature leaves. Yellowish-green ground color, 144A, with dark reddish brown spots and blotches, close to 187A. Young foliage, lower surface: Similar to upper surface, but lighter close to 144A; blotches, dulled, close to 187A. Mature, upper surface: Dark green with dark brownish red spots and blotches. Dark brownish red color closest to 183A/183B to 187A/187B. Dark green color closest to 146A/147A. Mature, lower surface: Dulled compared to upper surface, spots and blotches are fainter. Petiole length: on average, about 16 cm. Petiole color: Medium, 144A, to light green.

Flower description: Flowers are only formed on plants grown in an aerial environment. Plants form flowers under long photoperiods. Flowers formed are androgynous. Inflorescences racemose, above the leaves, erect to slighty decumbent, with 5 to 6 whorls with numerous flowers and vegetative proliferations; rachis rounded between whorls. Bracts acuminate, to about 1.5 cm long and about 4 mm wide. Flowers about 4 cm in width, slightly patellate, pedicels about 5.5 cm long. Sepals, three in number, brown, about 6 mm by 4 mm. Petals, three in number, white, slightly overlapping, slightly emarginate, about 2 cm by 2.5 cm. Stamens, about 16 in number, anthers about 2.5 mm in length and filaments about 3 mm in length. Carpels numerous.

Disease resistance: No resistance to diseases has been noted.

Seed development: Seed development has not been observed.

It is claimed:

1. A new and distinct cultivar of Echinodorus plant named 'Red Flame', as illustrated and described.

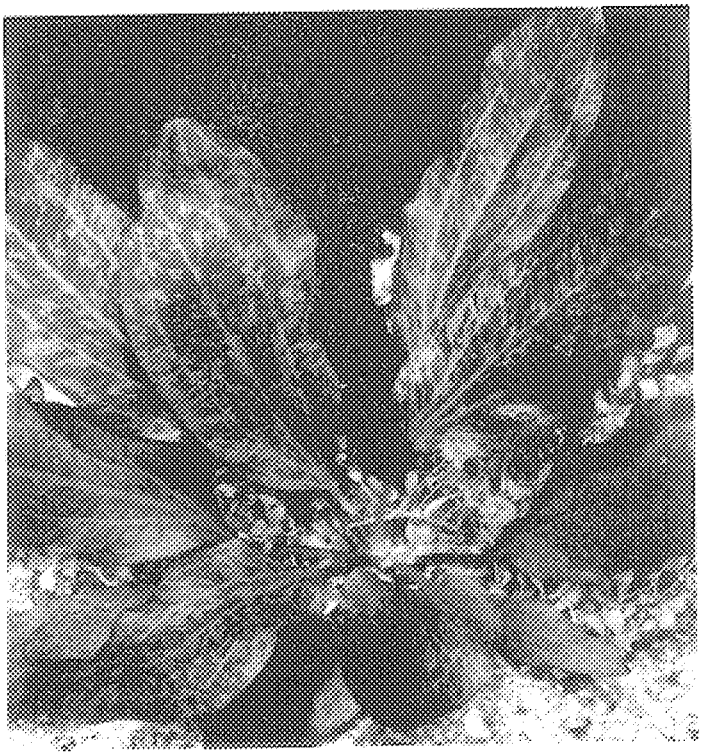

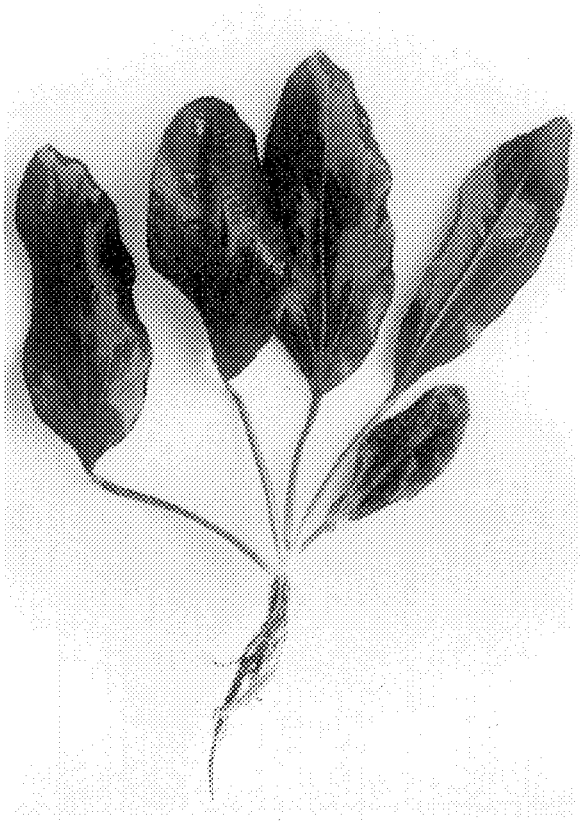

* * * * *